United States Patent
Sasaki

(10) Patent No.: US 10,362,930 B2
(45) Date of Patent: Jul. 30, 2019

(54) ENDOSCOPE APPARATUS

(71) Applicant: OLYMPUS CORPORATION, Tokyo (JP)

(72) Inventor: Hiroshi Sasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 487 days.

(21) Appl. No.: 15/169,934

(22) Filed: Jun. 1, 2016

(65) Prior Publication Data

US 2016/0270643 A1  Sep. 22, 2016

Related U.S. Application Data

(63) Continuation of application No. PCT/JP2014/073243, filed on Sep. 3, 2014.

(30) Foreign Application Priority Data

Dec. 18, 2013 (JP) ................ 2013-261650

(51) Int. Cl.
*A61B 1/00* (2006.01)
*A61B 1/04* (2006.01)
(Continued)

(52) U.S. Cl.
CPC ........ *A61B 1/0646* (2013.01); *A61B 1/00009* (2013.01); *A61B 1/00045* (2013.01);
(Continued)

(58) Field of Classification Search
CPC ............. A61B 1/0646; A61B 1/00045; A61B 1/00112; A61B 1/0052; A61B 1/06;
(Continued)

(56) References Cited

U.S. PATENT DOCUMENTS 4,860,094 A * 8/1989 Hibino ............... A61B 1/00059
   600/109
4,878,113 A * 10/1989 Nakamura ........... A61B 1/0638
   348/71
(Continued)

FOREIGN PATENT DOCUMENTS

CN 102188219 A 9/2011
JP 60089187 A 5/1985
(Continued)

OTHER PUBLICATIONS

Japanese Office Action dated Jun. 27, 2017 in Japanese Patent Application No. 2013-261650.
(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An endoscope apparatus includes: a light source unit that emits white illumination light or narrow band illumination light; an image sensor having pixels; a filter unit arranged corresponding to the pixels and including filters having a filter for passing blue light, and a filter for passing the blue light and one of green light and red light, the number of the filters for passing the green light being not less than half of the number of all the filters of the filter unit, and the number of the filters for passing the blue light being not less than the number of the filters for passing the green light; a selecting unit that selects, from the pixels, a luminance component pixel depending on types of illumination light; and a demosaicing processing unit that generates a color image signal having color components based on the luminance component pixel.

6 Claims, 8 Drawing Sheets

(51) Int. Cl.
  *A61B 1/06*    (2006.01)
  *G02B 23/24*   (2006.01)
  *A61B 1/005*   (2006.01)
  *A61B 1/015*   (2006.01)
  *A61B 1/018*   (2006.01)
  *A61B 1/05*    (2006.01)
  *G06T 3/40*    (2006.01)
  *H04N 9/04*    (2006.01)

(52) U.S. Cl.
  CPC ........ *A61B 1/0052* (2013.01); *A61B 1/00163* (2013.01); *A61B 1/00186* (2013.01); *A61B 1/015* (2013.01); *A61B 1/018* (2013.01); *A61B 1/051* (2013.01); *A61B 1/0638* (2013.01); *A61B 1/0661* (2013.01); *G02B 23/2469* (2013.01); *G06T 3/4015* (2013.01); *H04N 9/045* (2013.01); *A61B 1/043* (2013.01); *H04N 2209/046* (2013.01)

(58) Field of Classification Search
  CPC . A61B 1/0638; A61B 1/0676; A61B 1/00163; A61B 1/00186; A61B 1/051
  USPC ........................................................ 600/109
  See application file for complete search history.

(56) References Cited

U.S. PATENT DOCUMENTS

| | | | | | |
|---|---|---|---|---|---|
| 4,885,634 | A * | 12/1989 | Yabe | ................ | A61B 1/00039 348/71 |
| 5,408,263 | A * | 4/1995 | Kikuchi | ............ | A61B 1/00059 348/223.1 |
| 5,852,468 | A * | 12/1998 | Okada | .................... | H04N 9/045 348/272 |
| 6,476,865 | B1 * | 11/2002 | Gindele | ................ | H04N 9/045 348/273 |
| 8,723,937 | B2 | 5/2014 | Sasaki | | |
| 9,282,302 | B2 * | 3/2016 | Uchihara | ............... | H04N 9/646 |
| 9,319,601 | B2 * | 4/2016 | He | ........................... | H04N 5/30 |
| 2005/0154262 | A1 * | 7/2005 | Banik | ............ | A61B 1/00059 600/179 |
| 2005/0197536 | A1 * | 9/2005 | Banik | ................ | A61B 1/00059 600/179 |
| 2005/0212934 | A1 * | 9/2005 | Hoshuyama | ........... | H04N 9/045 348/272 |
| 2005/0228231 | A1 * | 10/2005 | MacKinnon | ............. | A61B 1/05 600/180 |
| 2006/0232668 | A1 * | 10/2006 | Horn | ...................... | A61B 1/041 348/71 |
| 2008/0239070 | A1 | 10/2008 | Westwick et al. | | |
| 2009/0021578 | A1 * | 1/2009 | Yamazaki | .......... | A61B 1/0638 348/65 |
| 2009/0115870 | A1 * | 5/2009 | Sasaki | .................... | H04N 9/045 348/223.1 |
| 2009/0242797 | A1 * | 10/2009 | Yazdanfar | ......... | A61B 1/00165 250/458.1 |
| 2011/0112362 | A1 * | 5/2011 | Minetoma | ................ | A61B 1/05 600/109 |
| 2011/0176730 | A1 | 7/2011 | Sasaki | | |
| 2011/0228064 | A1 * | 9/2011 | Sasaki | ................ | A61B 1/00096 348/65 |
| 2011/0273548 | A1 * | 11/2011 | Uchiyama | .......... | A61B 1/00009 348/68 |
| 2012/0105612 | A1 * | 5/2012 | Yoshino | ............. | A61B 1/00009 348/65 |
| 2012/0147165 | A1 * | 6/2012 | Yoshino | ............. | H04N 5/23212 348/65 |
| 2012/0197077 | A1 * | 8/2012 | Kaku | ................. | A61B 1/00009 600/109 |
| 2012/0265041 | A1 * | 10/2012 | Yamaguchi | ........ | A61B 1/00004 600/328 |
| 2013/0152020 | A1 * | 6/2013 | Nishiyama | ......... | A61B 1/00009 715/835 |
| 2013/0258082 | A1 | 10/2013 | Uchihara | | |
| 2016/0270642 | A1 * | 9/2016 | Morita | ..................... | A61B 1/04 |
| 2016/0270643 | A1 * | 9/2016 | Sasaki | ................ | A61B 1/00009 |
| 2017/0014055 | A1 * | 1/2017 | Otani | .................... | A61B 5/1459 |
| 2017/0018083 | A1 * | 1/2017 | Kuramoto | ............ | A61B 5/1032 |
| 2017/0230624 | A1 * | 8/2017 | Hanawa | ................... | H04N 9/07 |
| 2017/0231469 | A1 * | 8/2017 | Kaku | ................. | A61B 1/00006 600/479 |
| 2017/0251932 | A1 * | 9/2017 | Kaku | ................. | A61B 1/00009 |
| 2017/0319051 | A1 * | 11/2017 | Kuriyama | .......... | A61B 1/00006 |
| 2017/0360287 | A1 * | 12/2017 | Morimoto | ............ | A61B 1/0638 |
| 2018/0007256 | A1 * | 1/2018 | Yoshino | ................. | G02B 23/24 |
| 2018/0020903 | A1 * | 1/2018 | Saito | ........................ | A61B 1/04 382/128 |
| 2018/0033142 | A1 * | 2/2018 | Morita | ..................... | A61B 1/04 |
| 2018/0042468 | A1 * | 2/2018 | Teramura | ............. | G06T 7/0012 |
| 2018/0049679 | A1 * | 2/2018 | Chiba | ............... | A61B 1/00009 |
| 2018/0214005 | A1 * | 8/2018 | Ebata | ....................... | A61B 1/04 |
| 2018/0218499 | A1 * | 8/2018 | Kamon | ..................... | A61B 1/00 |
| 2018/0242893 | A1 * | 8/2018 | Saito | ........................ | A61B 1/00 |
| 2018/0249889 | A1 * | 9/2018 | Imai | .................. | A61B 1/00009 |

FOREIGN PATENT DOCUMENTS

| | | |
|---|---|---|
| JP | H08-237672 A | 9/1996 |
| JP | 2001186534 A | 7/2001 |
| JP | 2008-035470 A | 2/2008 |
| JP | 2011-143100 A | 7/2011 |
| JP | 2012-170640 A | 9/2012 |
| JP | 2013-208284 A | 10/2013 |

OTHER PUBLICATIONS

International Search Report dated Nov. 4, 2014 issued in PCT/JP2014/073243.
Chinese Office Action dated Jan. 30, 2018 in Chinese Patent Application No. 201480065889.X.
Extended Supplementary European Search Report dated Aug. 25, 2017 in European Patent Application No. 14 87 1429.8.

* cited by examiner

FIG.3

| $P_{11}$ | $P_{12}$ | $P_{13}$ | $P_{14}$ | ... |
|---|---|---|---|---|
| $P_{21}$ | $P_{22}$ | $P_{23}$ | $P_{24}$ | ... |
| $P_{31}$ | $P_{32}$ | $P_{33}$ | $P_{34}$ | ... |
| $P_{41}$ | $P_{42}$ | $P_{43}$ | $P_{44}$ | ... |
| ⋮ | ⋮ | ⋮ | ⋮ | ⋱ |

| $B_{11}$ | $G_{12}$ | $B_{13}$ | $G_{14}$ | ... |
|---|---|---|---|---|
| $G_{21}$ | $Mg_{22}$ | $G_{23}$ | $Mg_{24}$ | ... |
| $B_{31}$ | $G_{32}$ | $B_{33}$ | $G_{34}$ | ... |
| $G_{41}$ | $Mg_{42}$ | $G_{43}$ | $Mg_{44}$ | ... |
| ⋮ | ⋮ | ⋮ | ⋮ | ⋱ |

FIG.7

| | U2 | | |
|---|---|---|---|
| $B_{11}$ | $Cy_{12}$ | $B_{13}$ | $Cy_{14}$ | ... |
| $Cy_{21}$ | $R_{22}$ | $Cy_{23}$ | $R_{24}$ | ... |
| $B_{31}$ | $Cy_{32}$ | $B_{33}$ | $Cy_{34}$ | ... |
| $Cy_{41}$ | $R_{42}$ | $Cy_{43}$ | $R_{44}$ | ... |
| ⋮ | ⋮ | ⋮ | ⋮ | ⋱ |

FIG.8

| | U3 | | |
|---|---|---|---|
| $B_{11}$ | $Cy_{12}$ | $B_{13}$ | $Cy_{14}$ | ... |
| $Cy_{21}$ | $Mg_{22}$ | $Cy_{23}$ | $Mg_{24}$ | ... |
| $B_{31}$ | $Cy_{32}$ | $B_{33}$ | $Cy_{34}$ | ... |
| $Cy_{41}$ | $Mg_{42}$ | $Cy_{43}$ | $Mg_{44}$ | ... |
| ⋮ | ⋮ | ⋮ | ⋮ | ⋱ |

FIG.9

| | U4 | | | |
|---|---|---|---|---|
| $B_{11}$ | $Cy_{12}$ | $B_{13}$ | $Cy_{14}$ | ... |
| $Cy_{21}$ | $W_{22}$ | $Cy_{23}$ | $W_{24}$ | ... |
| $B_{31}$ | $Cy_{32}$ | $B_{33}$ | $Cy_{34}$ | ... |
| $Cy_{41}$ | $W_{42}$ | $Cy_{43}$ | $W_{44}$ | ... |
| ⋮ | ⋮ | ⋮ | ⋮ | ⋱ |

FIG.10

| | | | U5 | | | | | |
|---|---|---|---|---|---|---|---|---|
| $B_{11}$ | $G_{12}$ | $Mg_{13}$ | $G_{14}$ | $B_{15}$ | $G_{16}$ | $Mg_{17}$ | $G_{18}$ | ... |
| $G_{21}$ | $Mg_{22}$ | $G_{23}$ | $B_{24}$ | $G_{25}$ | $Mg_{26}$ | $G_{27}$ | $B_{28}$ | ... |
| $Mg_{31}$ | $G_{32}$ | $B_{33}$ | $G_{34}$ | $Mg_{35}$ | $G_{36}$ | $B_{37}$ | $G_{38}$ | ... |
| $G_{41}$ | $B_{42}$ | $G_{43}$ | $Mg_{44}$ | $G_{45}$ | $B_{46}$ | $G_{47}$ | $Mg_{48}$ | ... |
| $B_{51}$ | $G_{52}$ | $Mg_{53}$ | $G_{54}$ | $B_{55}$ | $G_{56}$ | $Mg_{57}$ | $G_{58}$ | ... |
| $G_{61}$ | $Mg_{62}$ | $G_{63}$ | $B_{64}$ | $G_{65}$ | $Mg_{66}$ | $G_{67}$ | $B_{68}$ | ... |
| $Mg_{71}$ | $G_{72}$ | $B_{73}$ | $G_{74}$ | $Mg_{75}$ | $G_{76}$ | $B_{77}$ | $G_{78}$ | ... |
| $G_{81}$ | $B_{82}$ | $G_{83}$ | $Mg_{84}$ | $G_{85}$ | $B_{86}$ | $G_{87}$ | $Mg_{88}$ | ... |
| ⋮ | ⋮ | ⋮ | ⋮ | ⋮ | ⋮ | ⋮ | ⋮ | ⋱ |

FIG.11

| | U6 | | | | | | | |
|---|---|---|---|---|---|---|---|---|
| $B_{11}$ | $W_{12}$ | $Mg_{13}$ | $W_{14}$ | $B_{15}$ | $W_{16}$ | $Mg_{17}$ | $W_{18}$ | ... |
| $W_{21}$ | $Mg_{22}$ | $W_{23}$ | $B_{24}$ | $W_{25}$ | $Mg_{26}$ | $W_{27}$ | $B_{28}$ | ... |
| $Mg_{31}$ | $W_{32}$ | $B_{33}$ | $W_{34}$ | $Mg_{35}$ | $W_{36}$ | $B_{37}$ | $W_{38}$ | ... |
| $W_{41}$ | $B_{42}$ | $W_{43}$ | $Mg_{44}$ | $W_{45}$ | $B_{46}$ | $W_{47}$ | $Mg_{48}$ | ... |
| $B_{51}$ | $W_{52}$ | $Mg_{53}$ | $W_{54}$ | $B_{55}$ | $W_{56}$ | $Mg_{57}$ | $W_{58}$ | ... |
| $W_{61}$ | $Mg_{62}$ | $W_{63}$ | $B_{64}$ | $W_{65}$ | $Mg_{66}$ | $W_{67}$ | $B_{68}$ | ... |
| $Mg_{71}$ | $W_{72}$ | $B_{73}$ | $W_{74}$ | $Mg_{75}$ | $W_{76}$ | $B_{77}$ | $W_{78}$ | ... |
| $W_{81}$ | $B_{82}$ | $W_{83}$ | $Mg_{84}$ | $W_{85}$ | $B_{86}$ | $W_{87}$ | $Mg_{88}$ | ... |
| ⋮ | ⋮ | ⋮ | ⋮ | ⋮ | ⋮ | ⋮ | ⋮ | ⋱ |

ENDOSCOPE APPARATUS

CROSS-REFERENCE TO RELATED APPLICATIONS

This application is a continuation of PCT international application Ser. No. PCT/JP2014/073243 filed on Sep. 3, 2014 which designates the United States, incorporated herein by reference, and which claims the benefit of priority from Japanese Patent Application No. 2013-261650, filed on Dec. 18, 2013, incorporated herein by reference.

BACKGROUND

1. Technical Field

The disclosure relates to an endoscope apparatus configured to be introduced into a living body to acquire images within the living body.

2. Related Art

Conventionally, endoscope apparatuses are widely used for various examinations in the medical field and industrial field. Among these endoscope apparatuses, a medical endoscope apparatus is capable of acquiring in-vivo images within a body cavity without incision of a subject, by inserting an elongated flexible insertion part with an image sensor having a plurality of pixels provided at a distal end into the body cavity of the subject such as a patient. Therefore, the medical endoscope apparatus imposes a light burden on the subject, and is coming into wide use.

As observation methods of such an endoscope apparatus, a white light imaging (WLI) method using white illumination light (white illumination light), and a narrow band imaging (NBI) method using illumination light including two kinds of narrow band light included in wavelength bands of blue light and green light, respectively (narrow band illumination light) are already widely known in the technical field. Among these methods, the narrow band imaging method may obtain an image with a highlighted capillary vessel and mucous membrane fine pattern and the like that exist in a mucous membrane surface layer of a living body (living body surface layer). Such a narrow band imaging method enables more accurate detection of a lesion in the mucous membrane surface layer of a living body. Regarding such observation methods of an endoscope apparatus, it is desired to switch between the white light imaging method and the narrow band imaging method for observation.

In order to acquire an image captured with a single-chip image sensor for generating and displaying a color image under the aforementioned observation methods, on a light-receiving surface of the image sensor is provided a color filter in which filters that respectively pass light of red (R), green (G), green (G), and blue (B) wavelength bands are arranged in each pixel as one filter unit, which is commonly referred to as the Bayer arrangement. In this case, each pixel receives light of the wavelength band that passes through the filter, and generates an electric signal of a color component according to the light of the wavelength band. Therefore, in processing for generating a color image, interpolation processing is performed in each pixel for interpolating a signal value of a missing color component that fails to pass through the filter. Such interpolation processing is referred to as demosaicing processing (for example, refer to Japanese Patent Application Laid-open No. 8-237672).

SUMMARY

In some embodiments, an endoscope apparatus includes: a light source unit configured to emit one of white illumination light and narrow band illumination light, the white illumination light including red wavelength band light, green wavelength band light, and blue wavelength band light, and the narrow band illumination light having a narrow wavelength band included in each of the blue wavelength band light and the green wavelength band light; an image sensor having a plurality of pixels arranged in a lattice pattern, each of which is configured to receive light, the image sensor being configured to perform photoelectric conversion on the light received by each of the plurality of pixels to generate an electric signal; a color filter including a filter unit arranged corresponding to the plurality of pixels, the filter unit including a plurality of filters having at least a filter for passing the blue wavelength band light, and a filter for passing the blue wavelength band light and at least one of the green wavelength band light and the red wavelength band light, the number of the filters for passing the green wavelength band light being equal to or greater than half of the number of all the filters of the filter unit, and the number of the filters for passing the blue wavelength band light being equal to or greater than the number of the filters for passing the green wavelength band light; a luminance component pixel selecting unit configured to select, from the plurality of pixels, a luminance component pixel for receiving light of a luminance component depending on types of illumination light the light source unit emits; and a demosaicing processing unit configured to generate a color image signal having a plurality of color components based on the luminance component pixel selected by the luminance component pixel selecting unit.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 3 is a schematic view illustrating a pixel layout of an image sensor according to the embodiment of the present invention;

FIG. 4 is a schematic view illustrating an example of a configuration of a color filter according to the embodiment of the present invention;

FIG. 7 is a schematic view illustrating the configuration of the color filter according to a first modification of the embodiment of the present invention;

FIG. 8 is a schematic view illustrating the configuration of the color filter according to a second modification of the embodiment of the present invention;

FIG. 9 is a schematic view illustrating the configuration of the color filter according to a third modification of the embodiment of the present invention;

FIG. 10 is a schematic view illustrating the configuration of the color filter according to a fourth modification of the embodiment of the present invention; and FIG. 11 is a schematic view illustrating the configuration of the color filter according to a fifth modification of the embodiment of the present invention.

DETAILED DESCRIPTION

Reference will be made below to modes for carrying out the invention (hereinafter referred to as "embodiment(s)"). In the embodiments, a medical endoscope apparatus will be described that captures and displays an image within a body cavity of a subject, such as a patient. The invention is not limited by the embodiments. The same reference signs are used to designate the same elements throughout the drawings.

Figure 1:
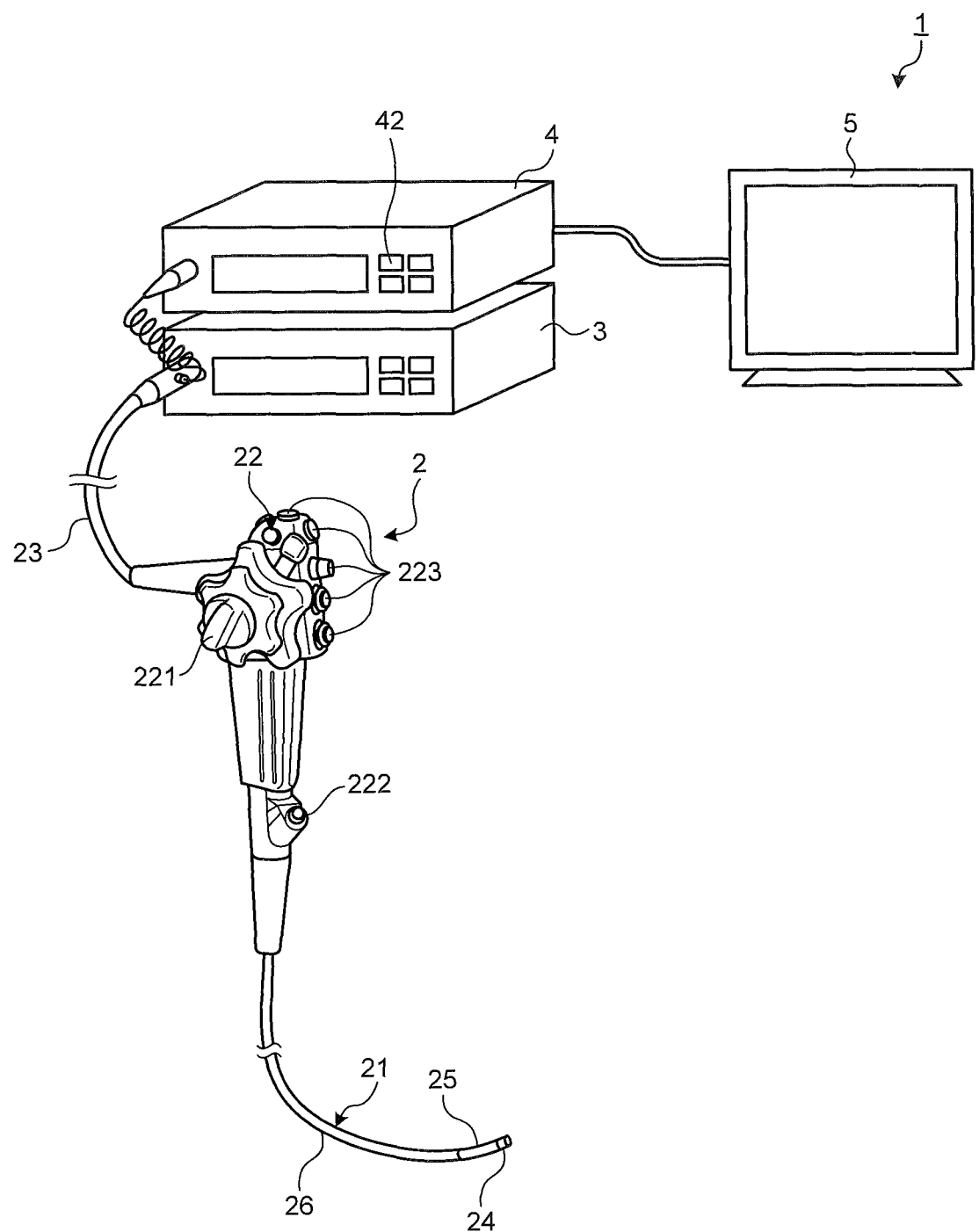
FIG. 1 is a diagram illustrating a schematic configuration of an endoscope apparatus according to an embodiment of the present invention.
Figure 2:
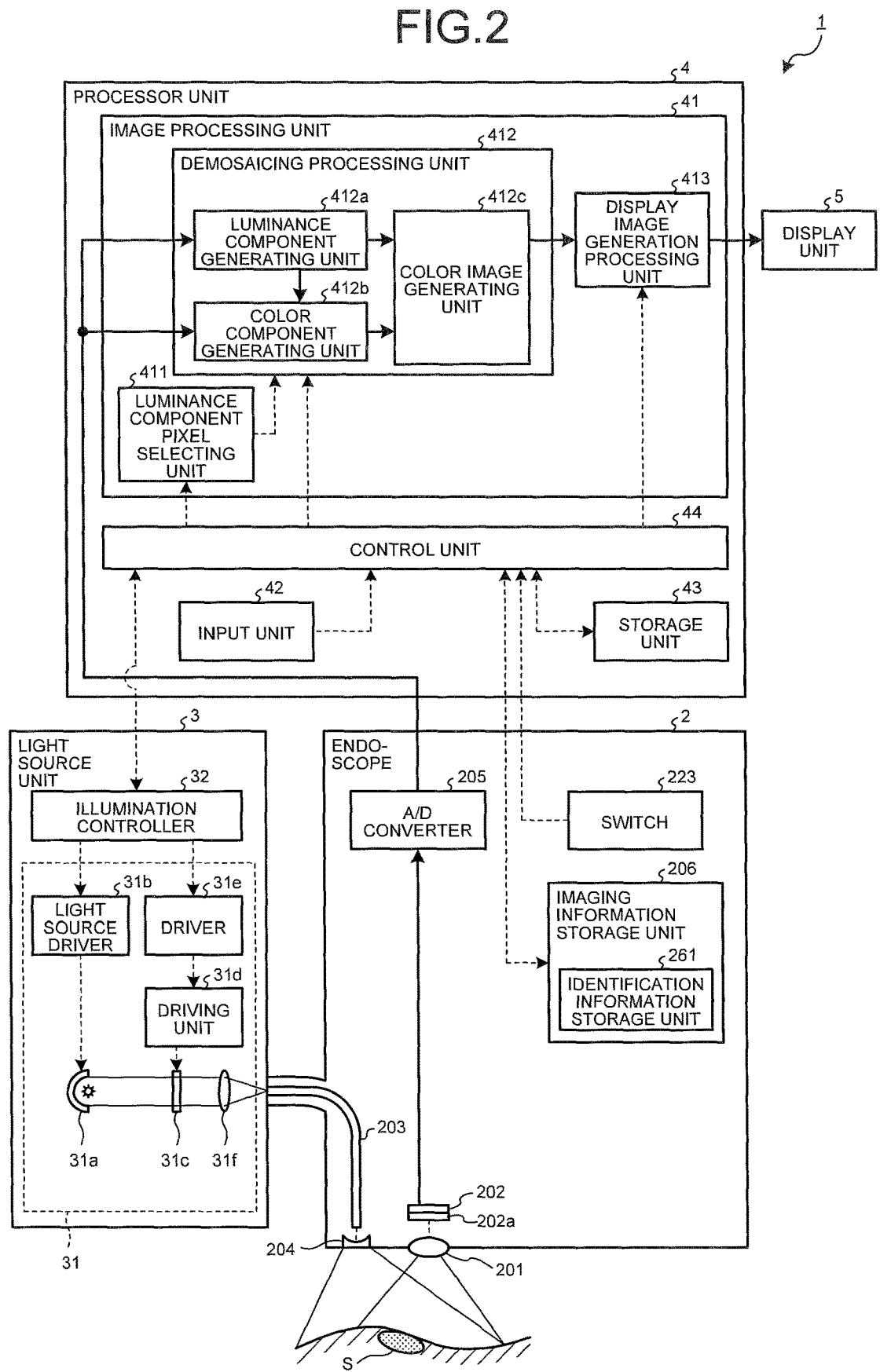
FIG. 2 is a schematic view illustrating the schematic configuration of the endoscope apparatus according to the embodiment of the present invention.

FIG. 1 is a diagram illustrating the schematic configuration of the endoscope apparatus according to the embodiment of the present invention. FIG. 2 is a schematic view illustrating the schematic configuration of the endoscope apparatus according to the embodiment. An endoscope apparatus 1 illustrated in FIG. 1 and FIG. 2 includes an endoscope 2 that captures an in-vivo image of an observed region to generate an electric signal by inserting an insertion part 21 into a body cavity of a subject, a light source unit 3 that generates illumination light to be emitted from a distal end of the endoscope 2, a processor unit 4 that applies predetermined image processing to the electric signal acquired by the endoscope 2, the processor unit 4 controlling overall operations of the endoscope apparatus 1 as a whole, and a display unit 5 that displays the in-vivo image to which the processor unit 4 applies the image processing. The endoscope apparatus 1 acquires the in-vivo image within the body cavity by inserting the insertion part 21 into the body cavity of the subject, such as a patient. A user, such as a doctor, observes the acquired in-vivo image to examine presence of a bleeding site or tumor site (lesion S), which is a region to be detected.

The endoscope 2 includes the flexible, elongated insertion part 21, an operating unit 22 which is connected to a proximal end side of the insertion part 21 and receives input of various operating signals, and a universal cord 23 extending in a direction different from a direction in which the insertion part 21 extends from the operating unit 22, the universal cord 23 incorporating various cables that connect to the light source unit 3 and the processor unit 4.

The insertion part 21 includes a distal end part 24 incorporating an image sensor 202 in which light-receiving pixels (photo diodes) are arranged in a lattice pattern (in a matrix), the image sensor 202 generating an image signal by applying photoelectric conversion to the light received by the pixels, a bending part 25 which includes a plurality of curve pieces and curves freely, and a long flexible-tube part 26 which is connected to a proximal end side of the bending part 25 and has flexibility.

The operating unit 22 includes a bending knob 221 that causes the bending part 25 to bend in a vertical direction and a horizontal direction, a treatment tool insertion part 222 through which a treatment tool, such as living body forceps, electric knife, and inspecting probe, is inserted into a body cavity of a subject, and a plurality of switches 223 that input signals such as an instruction signal for causing the light source unit 3 to perform switching operations of illumination light, an operation instruction signal for the treatment tool and an external instrument connected to the processor unit 4, a water supply instruction signal for supplying water, and a suction instruction signal for performing suction. The treatment tool inserted through the treatment tool insertion part 222 travels through a treatment tool channel (not illustrated) provided at a distal end of the distal end part 24 and goes out from an aperture (not illustrated).

The universal cord 23 incorporates at least a light guide 203 and a cable assembly into which one or more signal lines are combined. The cable assembly is signal lines that transmit and receive signals between the endoscope 2 and the light source unit 3, and the processor unit 4. The cable assembly includes a signal line for transmitting and receiving setting data, a signal line for transmitting and receiving an image signal, and a signal line for transmitting and receiving a drive timing signal for driving the image sensor 202.

In addition, the endoscope 2 includes an imaging optical system 201, the image sensor 202, the light guide 203, an illumination lens 204, an A/D converter 205, and an imaging information storage unit 206.

The imaging optical system 201 is provided at the distal end part 24, and collects at least light from the observed region. The imaging optical system 201 includes one or more lenses. Note that the imaging optical system 201 may be provided with an optical zoom mechanism for changing an angle of view and a focus mechanism for changing a focal point.

The image sensor 202 is provided perpendicularly to an optical axis of the imaging optical system 201, performs photoelectric conversion on an image of light formed by the imaging optical system 201, and generates an electric signal (image signal). The image sensor 202 is implemented using a charge coupled device (CCD) image sensor, complementary metal oxide semiconductor (CMOS) image sensor, and the like.

FIG. 3 is a schematic view illustrating a pixel layout of the image sensor according to the embodiment. In the image sensor 202, a plurality of pixels for receiving light from the imaging optical system 201 are arranged in a lattice pattern (in a matrix). Then, the image sensor 202 performs photoelectric conversion on the light received by each pixel to generate an electric signal (also referred to as an image signal and the like). This electric signal includes a pixel value (luminance value) and pixel position information of each pixel. In FIG. 3, a pixel arranged at i-th line and j-th row is denoted as a pixel $P_{ij}$.

The image sensor 202 is provided with a color filter 202a disposed between the imaging optical system 201 and the image sensor 202. The color filter 202a has a plurality of filters configured to pass light with individually set wavelength bands. The color filter 202a is provided on a light-receiving surface of the image sensor 202.

FIG. 4 is a schematic view illustrating an example of the configuration of the color filter according to the embodiment. According to the embodiment, the color filter 202a includes, for example, filter units U1 arranged two-dimensionally (in a matrix) according to arrangement of the pixels $P_{ij}$, the filter units U1 each including four filters arranged in a 2×2 matrix. The pixel $P_{ij}$ that is provided with the filter receives light of a wavelength band the filter passes. For example, the pixel $P_{ij}$ that is provided with the filter that passes light of a blue wavelength band receives the light of the blue wavelength band. Hereinafter, the pixel $P_{ij}$ that receives the light of the blue wavelength band is referred to as a B pixel. Similarly, the pixel that receives light of a green wavelength band is referred to as a G pixel, and the pixel that receives light of a red wavelength band is referred to as an R pixel.

The filter unit U1 here passes light of a blue (B) wavelength band $H_B$, green (G) wavelength band $H_G$, and red (R) wavelength band $H_R$. In addition, a plurality of filters are selected and arranged in the filter unit U1 so that the number of filters that pass light of the wavelength band $H_G$ may be equal to or greater than half of the number of all the filters that constitute the filter unit U1, and the number of filters that pass light of the wavelength band $H_B$ may be equal to or greater than the number of filters that pass light of the wavelength band $H_G$. The blue, green, and red wavelength bands $H_B$, $H_G$, and $H_R$ are, for example, 390 nm to 500 nm, 500 nm to 600 nm, and 600 nm to 700 nm, respectively.

As illustrated in this FIG. 4, the filter unit U1 according to the embodiment includes one B filter that passes light of the wavelength band $H_B$, two G filters that pass light of the wavelength band $H_G$, and one Mg filter that passes light of the wavelength band $H_B$ and the wavelength band $H_R$. Hereinafter, when the B filter is provided at a position corresponding to the pixel $P_{ij}$, this B filter is denoted as $B_{ij}$. Similarly, when the G filter is provided at a position corresponding to the pixel $P_{ij}$, this G filter is denoted as $G_{ij}$, and when the Mg filter is provided, this Mg filter is denoted as $Mg_{ij}$. Note that when light of the wavelength band $H_B$ (blue light) and light of the wavelength band $H_R$ (red light) are mixed, light of magenta (Mg) will be generated.

In the filter unit U1, the number of filters that pass light of the wavelength band $H_G$ (G filters) is two, and the number of filters that pass light of the wavelength band $H_B$ (B filter and Mg filter) is two.

Figure 5:
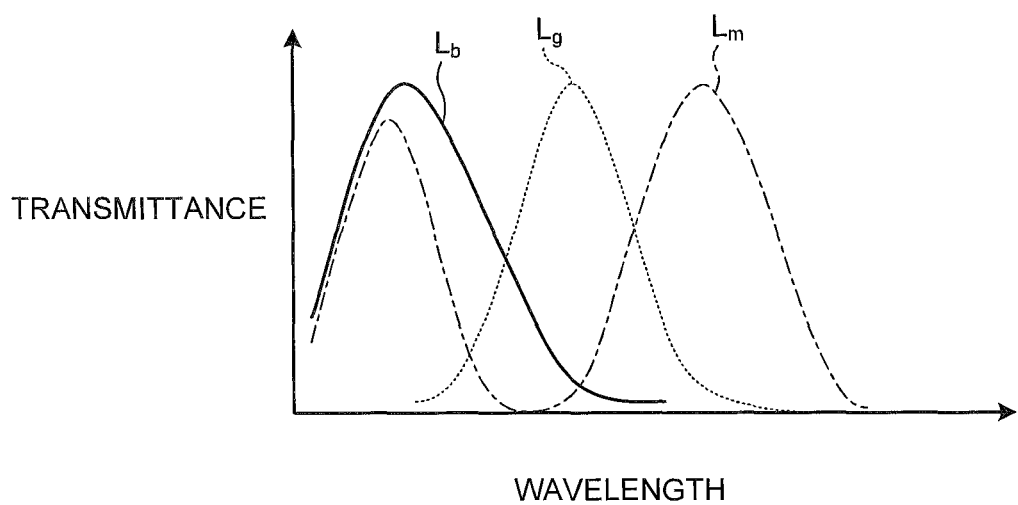
FIG. 5 is a diagram illustrating an example of a characteristic of each filter of the color filter according to the embodiment of the present invention.

FIG. 5 is a diagram illustrating an example of characteristics of each filter of the color filter according to the embodiment, and is a diagram illustrating a relationship between the wavelength of light and transmittance of each filter. In FIG. 5, transmittance curves are normalized so that the maximum value of the transmittance of each filter may become identical. A curved line $L_b$ (solid line) illustrated in FIG. 5 represents the transmittance curve of the B filter, a curved line $L_g$ (dashed line) represents the transmittance curve of the G filter, and a curved line $L_m$ (alternate long and short dash line) represents the transmittance curve of the Mg filter.

The B filter passes light of the wavelength band $H_B$. The Mg filter passes light of the wavelength band of magenta, which is a complementary color to green. In other words, the Mg filter absorbs light of the wavelength band $H_G$, passes light of the wavelength band $H_B$, and passes light of the wavelength band $H_R$. The G filter passes light of the wavelength band $H_G$. Note that in the description, the complementary color refers to a color made of light that includes at least two wavelength bands among the wavelength bands $H_B$, $H_G$, and $H_R$.

Returning to description of FIG. 1 and FIG. 2, the light guide 203 is configured by a glass fiber and the like, and constitutes a light guide path for light emitted from the light source unit 3.

The illumination lens 204 is provided at a distal end of the light guide 203, diffuses light guided by the light guide 203, and emits the light to outside of the distal end part 24.

The A/D converter 205 performs A/D conversion on the electric signal generated by the image sensor 202, and outputs the converted electric signal to the processor unit 4.

The imaging information storage unit 206 stores various programs for operating the endoscope 2, and data including various parameters necessary for operations of the endoscope 2, identification information of the endoscope 2, and the like. In addition, the imaging information storage unit 206 includes an identification information storage unit 261 that stores identification information. The identification information includes information unique to the endoscope 2 (ID), model year, specification information, transmission method, filter arrangement information related to the color filter 202a, and the like. The imaging information storage unit 206 is implemented using a flash memory and the like.

Next, the configuration of the light source unit 3 will be described. The light source unit 3 includes an illumination unit 31 and an illumination controller 32.

The illumination unit 31 switches and emits a plurality of beams of illumination light that differ from each other in wavelength band, under control of the illumination controller 32. The illumination unit 31 includes a light source 31a, a light source driver 31b, a switching filter 31c, a driving unit 31d, a driver 31e, and a condenser lens 31f.

The light source 31a emits white illumination light including light of red, green, and blue wavelength bands $H_B$, $H_G$, and $H_R$, respectively, under control of the illumination controller 32. The white illumination light generated by the light source 31a travels through the switching filter 31c, the condenser lens 31f, and the light guide 203, and is emitted outside from the distal end part 24. The light source 31a is implemented using a light source that emits white light, such as a white LED and a xenon lamp.

The light source driver 31b causes the light source 31a to emit the white illumination light by supplying an electric current to the light source 31a under control of the illumination controller 32.

The switching filter 31c passes only blue narrow band light and green narrow band light out of the white illumination light emitted by the light source 31a. The switching filter 31c is removably disposed on an optical path of the white illumination light emitted by the light source 31a under the control of the illumination controller 32. The switching filter 31c is disposed on the optical path of the white illumination light to pass only rays of light of two narrow bands. Specifically, the switching filter 31c passes narrow band illumination light including light of a narrow band $T_B$ (for example, 390 nm to 445 nm) in the wavelength band $H_B$, and light of a narrow band $T_G$ (for example, 530 nm to 550 nm) in the wavelength band $H_G$. The narrow bands $T_B$ and $T_G$ are wavelength bands of blue light and green light, respectively, which are easily absorbed by hemoglobin within blood. Note that at least a wavelength band of 405 nm to 425 nm may be included as the narrow band $T_B$. The light emitted with the wavelength limited to this band is referred to as a narrow band illumination light, and observation of an image with the narrow band illumination light is referred to as a narrow band imaging (NBI) method.

The driving unit 31d is configured by a stepping motor, a DC motor, and the like, and causes the switching filter 31c to be located on or to be removed from the optical path of the light source 31a.

The driver 31e supplies a predetermined electric current to the driving unit 31d under control of the illumination controller 32.

The condenser lens 31f collects the white illumination light emitted by the light source 31a or the narrow band illumination light that passes through the switching filter 31c, and emits the white illumination light or the narrow band illumination light to outside of the light source unit 3 (light guide 203).

The illumination controller 32 controls the light source driver 31b to perform on-off operation of the light source 31a, and controls the driver 31e to cause the switching filter 31c to be located on or to be removed from the optical path of the light source 31a and thereby to control types (bands) of illumination light emitted by the illumination unit 31.

Specifically, the illumination controller 32 causes the switching filter 31c to be inserted into and to be deviated from the optical path of the light source 31a to switch illumination light emitted from the illumination unit 31 to one of the white illumination light and the narrow band illumination light. In other words, the illumination controller 32 switches between the white light imaging (WLI) method using the white illumination light having the wavelength bands $H_B$, $H_G$, and $H_R$, and the narrow band imaging (NBI) method using the narrow band illumination light having the narrow bands $T_B$, $T_G$.

Next, the configuration of the processor unit 4 will be described. The processor unit 4 includes an image processing unit 41, an input unit 42, a storage unit 43, and a control unit 44.

The image processing unit 41 performs predetermined image processing based on the electric signal from the endoscope 2 (A/D converter 205), and generates image information to be displayed by the display unit 5. The image processing unit 41 includes a luminance component pixel selecting unit 411, a demosaicing processing unit 412, and a display image generation processing unit 413.

The luminance component pixel selecting unit 411 determines changeover operations of the illumination light by the illumination controller 32, that is, determines which of the white illumination light and the narrow band illumination light the illumination light emitted by the illumination unit 31 is. The luminance component pixel selecting unit 411 selects a luminance component pixel (pixel for receiving light of a luminance component) to be used by the demosaicing processing unit 412 according to the determined illumination light.

The demosaicing processing unit 412 includes a luminance component generating unit 412a, a color component generating unit 412b, and a color image generating unit 412c. The demosaicing processing unit 412 generates a color image signal by discriminating an interpolation direction from a correlation of color information of a plurality of pixels (pixel values) based on the luminance component pixel selected by the luminance component pixel selecting unit 411, and by performing interpolation based on the color information of the pixels located in a line in the discriminated interpolation direction.

The luminance component generating unit 412a discriminates the interpolation direction by using the pixel values generated by the luminance component pixel selected by the luminance component pixel selecting unit 411, interpolates the luminance component in pixels other than the luminance component pixel based on the discriminated interpolation direction, and generates the image signal that forms one sheet of image in which each pixel has a pixel value of the luminance component or an interpolated pixel value (hereinafter referred to as an interpolation value).

An example of processing for generating the luminance component by the luminance component generating unit 412a will be described. For example, when the luminance component pixel is a G pixel that receives light of a green wavelength band, the luminance component generating unit 412a discriminates the interpolation direction of a green component in a pixel to be interpolated at which the G pixel is missing (B pixel, or Mg pixel that receives light of a magenta wavelength band) by using an interpolation candidate value calculated based on the pixel values of the G pixels at positions adjacent to the pixel to be interpolated. In the embodiment, the interpolation direction is one of a vertical direction, horizontal direction, oblique direction, and no direction (hereinafter just referred to as oblique direction). For example, when a pixel $P_{22}$, which is an Mg pixel, is a pixel to be interpolated, the interpolation candidate value is calculated based on the pixel values of a pixel $P_{12}$, pixel $P_{21}$, pixel $P_{23}$, and pixel $P_{32}$, which are four G pixels. In this case, when the pixel value of the pixel $P_{12}$ is $g_{12}$ and the pixel value of the pixel $P_{32}$ is $g_{32}$, the vertical interpolation candidate value $g_{v22}$ of the missing G pixel is calculated by $g_{v22}=(g_{12}\ g_{32})/2$. Similarly, when the pixel value of the pixel $P_{21}$ is $g_{21}$ and the pixel value of the pixel $P_{23}$ is $g_{23}$, the horizontal interpolation candidate value $g_{h22}$ of the missing G pixel is calculated by $g_{h22}=(g_{21}+g_{23})/2$. The oblique interpolation candidate value $g_{a22}$ of the missing G pixel of the pixel $P_{22}$ is calculated by $g_{a22}=(g_{12}+g_{21}+g_{23}\ g_{32})/4$, by using four surrounding G pixels (pixel $P_{12}$, pixel $P_{21}$, pixel $P_{23}$, and pixel $P_{32}$).

Subsequently, the luminance component generating unit 412a calculates a color difference by taking difference between the pixel value of the pixel to be interpolated and the aforementioned interpolation candidate value. Also, the luminance component generating unit 412a calculates the color difference by taking difference between the pixel values of the pixels of the same type (for example, in FIG. 3, pixel $P_{24}$, pixel $P_{42}$, and pixel $P_{44}$ are applicable) positioned in the nearby eight directions (vertical direction, horizontal direction, or oblique direction) viewed from the pixel to be interpolated, and the interpolation candidate value. For example, when the pixel value of the pixel $P_{22}$ is $m_{22}$, the color difference from the vertical interpolation candidate value $g_{v22}$ will be $m_{22}$-$g_{v22}$. The luminance component generating unit 412a calculates the color difference between the pixel to be interpolated and each interpolation candidate value, and calculates the color difference between the pixels of the same type positioned in the nearby eight directions and each interpolation candidate value.

Subsequently, based on the color difference of the pixel to be interpolated and the color difference of the pixels of the same type in the nearby eight directions, the luminance component generating unit 412a calculates a differential absolute value sum (for example, a value obtained through assignment of weights in each direction according to a distance from the pixel to be interpolated) between the pixel to be interpolated and the pixels of the same type in each of the vertical direction, horizontal direction, and oblique direction. Then, the luminance component generating unit 412a calculates peripheral similarity in the vertical direction, horizontal direction, and oblique direction (correlation value) based on the differential absolute value sum. The luminance component generating unit 412a discriminates a direction with the smallest calculated value of the peripheral similarity (one of the vertical direction, horizontal direction, and oblique direction) as the interpolation direction, interpolates the luminance component (pixel value of the green component) based on the discriminated interpolation direction, and generates the image signal that forms one sheet of image in which each pixel has a pixel value $g_{ij}$ or interpolation value $g'_{ij}$ about the green component. For example, when the interpolation direction at the pixel $P_{22}$ illustrated in FIG. 3 is discriminated to be vertical, the interpolation value $g'_{22}$ will be $g'_{22}=g_{v22}$.

The color component generating unit 412b generates a color component other than the luminance component by using at least a pixel value of a pixel which is not selected as the luminance component pixel. For example, when the luminance component pixel is a G pixel, the color component generating unit 412b generates the image signal that forms one sheet of image that has the pixel value or interpolation value of a blue component and a magenta component for each color component, based on the pixel value g, interpolation value g° generated by the luminance component generating unit 412a, and pixel value b of a B pixel and pixel value m of an Mg pixel. Regarding details of the aforementioned luminance component processing and color component generation processing, the method described in Japanese Patent Application Laid-open No. 2008-35470 is used. Note that generation of the image signal of the Mg pixel is performed with the R pixel described in Japanese Patent Application Laid-open No. 2008-35470 replaced with the Mg pixel.

The color image generating unit 412c generates the color image signal that forms a color image by using the pixel value and interpolation value of the luminance component generated by the luminance component generating unit 412a, and the pixel value and interpolation value of the color component generated by the color component generating unit 412b. When a complementary color exists to light that passes through the color filter 202a, the color image generating unit 412c includes color separation processing of the complementary color. Specifically, since magenta exists in the embodiment, under the white light imaging method, the blue component is subtracted from this magenta component to separate the red component.

On the other hand, under the narrow band imaging method, since the Mg filter passes only the narrow band light of the narrow band $T_b$, the color image generating unit 412c generates the color image signal that forms the color image by using the blue component and the green component, and applying gain correction processing between the components and the like.

The display image generation processing unit 413 applies gradation conversion, magnification processing, or structure enhancement processing of structures, such as a capillary vessel of a mucous membrane surface layer and mucous membrane fine pattern, and the like to the color image signal generated by the color image generating unit 412c. After application of the predetermined processing, the display image generation processing unit 413 outputs the color image signal to the display unit 5 as a display image signal for display.

The image processing unit 41 performs OB clamp processing, gain adjustment processing, and the like, besides the aforementioned demosaicing processing. In the OB clamp processing, the image processing unit 41 applies processing for correcting an offset amount of a black level to the electric signal that is input from the endoscope 2 (A/D converter 205). In the gain adjustment processing, the image processing unit 41 applies adjustment processing of a brightness level to the image signal that undergoes demosaicing processing.

The input unit 42 is an interface for performing input from a user to the processor unit 4 and the like, and includes a power switch for turning on and off power supply, a mode switching button for switching an image capturing mode and other various modes, an illumination light switching button for switching illumination light of the light source unit 3, and the like.

The storage unit 43 records various programs for operating the endoscope apparatus 1, and data including various parameters and the like necessary for operations of the endoscope apparatus 1. Also, the storage unit 43 may store information regarding the endoscope 2, for example, a correspondence table between information unique to the endoscope 2 (ID) and information regarding filter arrangement of the color filter 202a. The storage unit 43 is implemented using a semiconductor memory, such as a flash memory and a DRAM (Dynamic Random Access Memory).

The control unit 44 is configured by a CPU and the like, and performs driving control on each element including the endoscope 2 and the light source unit 3, and input-output control of information into and from each element, and the like. The control unit 44 transmits setting data recorded in the storage unit 43 for imaging control (for example, pixels to be read) and a timing signal related to imaging timing and the like to the endoscope 2 via a predetermined signal line. The control unit 44 outputs color filter information (identification information) acquired via the imaging information storage unit 206 to the luminance component pixel selecting unit 411, and outputs information on a movement (arrangement) of the switching filter 31c.

Next, the display unit 5 will be described. The display unit 5 receives the display image signal generated by the processor unit 4 via a video cable, and displays an in-vivo image corresponding to the display image signal. The display unit 5 is configured by a liquid crystal display or an organic EL (Electro Luminescence) display.

Figure 6:
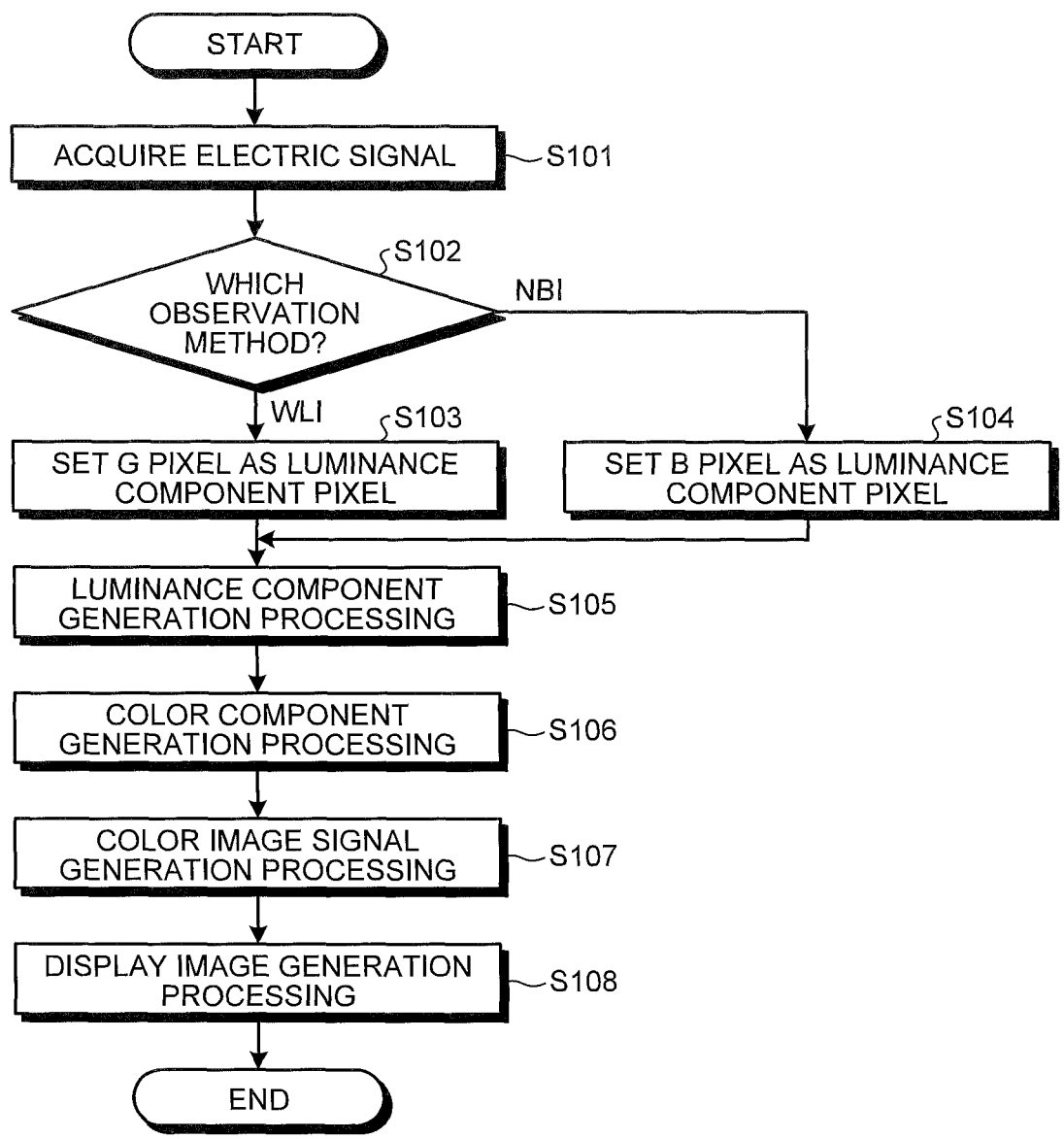
FIG. 6 is a flowchart illustrating signal processing to be performed by a processor unit of the endoscope apparatus according to the embodiment of the present invention.

FIG. 6 is a flowchart illustrating signal processing to be performed by the processor unit of the endoscope apparatus according to the embodiment. When the electric signal is acquired from the endoscope 2 (distal end part 24), the processor unit 4 outputs this electric signal to the demosaicing processing unit 412 (luminance component generating unit 412a and color component generating unit 412b) (step S101). The electric signal from the endoscope 2 is a signal that is generated by the image sensor 202 and contains Raw image data converted into a digital signal by the A/D converter 205.

When the electric signal is input into the demosaicing processing unit 412, the luminance component pixel selecting unit 411 determines under which observation method among the white light imaging method and the narrow band imaging method the input electric signal is generated (step S102). Specifically, the luminance component pixel selecting unit 411 determines under which observation method the input electric signal is generated based on a control signal from the control unit 44 (for example, information related to illumination light and information that indicates the observation method).

On determination that the input electric signal is generated under the white light imaging method (step S102; WLI), the luminance component pixel selecting unit 411 selects and sets the G pixel as the luminance component pixel, and outputs the set setting information to the demosaicing processing unit 412 (step S103). Specifically, the luminance component pixel selecting unit 411 outputs positional information on the G pixel to be set as the luminance component pixel based on the identification information (information on the color filter 202a), for example, information regarding line and row of the G pixel.

Meanwhile, on determination that the input electric signal is generated under the narrow band imaging method (step S102; NBI), the luminance component pixel selecting unit 411 selects and sets the B pixel as the luminance component pixel, and outputs the set setting information to the demosaicing processing unit 412 (step S104).

Here, under the narrow band imaging method, light of the wavelength band $H_R$ is not included in the narrow band illumination light. Accordingly, the Mg filter passes only light of the narrow band $T_B$, and the Mg pixel provided with the Mg filter substantially functions as the B pixel.

Therefore, the luminance component pixel selecting unit 411 outputs positional information on the B pixel and the Mg pixel which are set as the luminance component pixel based on the identification information (information on the color filter 202a provided in the distal end part 24), for example, information regarding line and row of the B pixel and the Mg pixel.

The luminance component generating unit 412a performs luminance component generation processing based on the setting information acquired from the luminance component pixel selecting unit 411 (step S105). Specifically, under the white light imaging method, the luminance component generating unit 412a discriminates the interpolation direction by using the pixel value of the G pixel, interpolates the luminance component in pixels other than the G pixel (B pixel and Mg pixel) based on the discriminated interpolation direction, and generates the image signal that forms one sheet of image in which each pixel has the pixel value or interpolation value of the green component. On the other hand, under the narrow band imaging method, the luminance component generating unit 412a discriminates the interpolation direction by using the pixel values of the B pixel and the Mg pixel, interpolates the luminance component in pixels other than the luminance component pixel (G pixel) based on the discriminated interpolation direction, and generates the image signal that forms one sheet of image in which each pixel has the pixel value or interpolation value of the blue component.

The color component generating unit 412b performs color component generation processing based on the setting information acquired from the luminance component pixel selecting unit 411 (step S106). Specifically, under the white light imaging method, the color component generating unit 412b generates one sheet of image that has the pixel value or interpolation value of the blue component and the magenta component for each color component, by using the pixel value and interpolation value of the luminance component generated by the luminance component generating unit 412a, and the pixel values of the B pixel and the Mg pixel. On the other hand, under the narrow band imaging method, the color component generating unit 412b generates the image signal that forms one sheet of image in which each pixel has the pixel value or interpolation value of the green component, by using the pixel value and interpolation value of the luminance component generated by the luminance component generating unit 412a, and the pixel value of the G pixel.

The color image generating unit 412c generates the color image signal that forms the color image by using the pixel value and interpolation value of the luminance component generated by the luminance component generating unit 412a, and the pixel value and interpolation value of the color component generated by the color component generating unit 412b (step S107). Specifically, under the white light imaging method, after subtraction of the blue component from the magenta component and separation of the red component, the color image generating unit 412c uses the luminance component (green component), blue component, and red component to generate the color image signal that forms the color image. On the other hand, under the narrow band imaging method, the color image generating unit 412c uses the luminance component (blue component) and the green component to generate the color image signal that forms the color image.

The display image generation processing unit 413 applies gradation conversion, magnification processing, or structure enhancement processing of structures, such as a capillary vessel of a mucous membrane surface layer and mucous membrane fine pattern, and the like to the color image signal generated by the color image generating unit 412c, to generate the display image signal for display (step S108). After application of the predetermined processing, the display image generation processing unit 413 outputs the color image signal to the display unit 5 as the display image signal.

Under the narrow band imaging method, it is preferable to set a pixel with a spatial frequency having more high-frequency component as the luminance component pixel. In this signal processing, by setting the B pixel as the luminance component pixel, the B pixel and Mg pixel on which light of the blue wavelength band enters will be selected as the luminance component pixel to perform direction discrimination interpolation. The reason for the aforementioned selection is that light of the blue narrow band $T_B$ depicts a capillary vessel image in a living body surface layer, light of the green narrow band $T_G$ depicts a thick blood vessel image which exists deeper than the living body surface layer (the deep blood vessel has an edge of a boundary portion that is blurred by scattering in a transparent living body mucous membrane, etc.), and that the B pixel has more high-frequency component as the spatial frequency than the G pixel. Accordingly, when viewed in the filter unit U1, since luminance component generation processing is performed by considering the diagonally arranged B pixel and the Mg pixel as the luminance component pixels, images of the narrow band imaging method may be obtained with high resolving power.

In addition, in this signal processing, under the white light imaging method, it is preferable to set the G pixel as the luminance component pixel in view of visual sensitivity characteristics (spatial frequency sensitivity to green is high), and the G pixel is set and selected as the luminance component pixel to perform direction discrimination interpolation. When viewed in the filter unit U1, since luminance component generation processing is performed by considering the diagonally arranged two G pixels as the luminance component pixels, images of the white light imaging method may be obtained with high resolving power.

The aforementioned endoscope apparatus 1 according to the embodiment includes the light source unit 3 that emits the white illumination light or narrow band illumination light as illumination light, the image sensor 202 in which the plurality of pixels are arranged, the color filter 202a in which the filters that pass light of predetermined wavelength are arranged, the demosaicing processing unit 412 that applies interpolation processing to generate color images, and the luminance component pixel selecting unit 411 that selects the luminance component pixel according to the illumination light. The color filter 202a is configured in units of the filter unit U1 that includes the B filter that passes light of the wavelength band $H_B$, G filter that passes light of the wavelength band $H_G$, and Mg filter that passes light of the wavelength bands $H_B$ and $H_R$. The filter unit U1 is adapted such that the number of filters that pass light of the wavelength band $H_G$ is equal to or greater than half of the number of filters that constitute the filter unit U1, and that the number of filters that pass light of the wavelength band $H_B$ is equal to or greater than the number of filters that pass light of the wavelength band $H_G$. Therefore, high-resolution images may be obtained in both observation methods of the white light imaging method and the narrow band imaging method.

In addition, according to the aforementioned present embodiment, since the luminance component pixel selecting unit 411 acquires positional information on the pixel that is set as the luminance component pixel based on the identification information from the control unit 44 (information on the color filter 202a), even if the endoscope 2 connected to the processor unit 4 (distal end part 24) is replaced with the endoscope 2 including the distal end part 24 with different filter arrangement of the color filter 202a, the positional information on the set luminance component pixel may be accurately specified.

First Modification

FIG. 7 is a schematic view illustrating the configuration of the color filter according to the first modification of the embodiment. The color filter according to the first modification includes two-dimensionally arranged filter units U2 that each include four filters arranged in a 2×2 matrix. Each of the filter units U2 includes one B filter that passes light of the wavelength band $H_B$, two Cy filters that pass light of the wavelength bands $H_B$ and $H_G$, and one R filter that passes light of the wavelength band $H_R$.

Each of the Cy filters passes light of a cyan wavelength band, which is a complementary color to red. In other words, the Cy filter absorbs light of the wavelength band $H_R$, passes light of the wavelength band $H_B$, and passes light of the wavelength band $H_G$. In the first modification, under the white light imaging method, the luminance component pixel selecting unit 411 sets, for example, a Cy pixel as the luminance component pixel. The color image generating unit 412c subtracts the blue component from a cyan component to separate the green component.

In the filter unit U2, the number of filters that pass light of the wavelength band $H_G$ (Cy filters) is two, and the number of filters that pass light of the wavelength band $H_B$ (B filter and Cy filters) is three.

Second Modification

FIG. 8 is a schematic view illustrating the configuration of the color filter according to the second modification of the embodiment. The color filter according to the second modification includes two-dimensionally arranged filter units U3 that each include four filters arranged in a 2×2 matrix. The filter unit U3 includes one B filter that passes light of the wavelength band $H_B$, two Cy filters that pass light of the wavelength bands $H_B$ and $H_G$, and one Mg filter that passes light of the wavelength bands $H_B$ and $H_R$.

In the filter unit U3, the number of filters that pass light of the wavelength band $H_G$ (Cy filters) is two, and the number of filters that pass light of the wavelength band $H_B$ (B filter, Cy filters, and Mg filter) is four.

Third Modification

FIG. 9 is a schematic view illustrating the configuration of the color filter according to the third modification of the embodiment. The color filter according to the third modification includes two-dimensionally arranged filter units U4 that each include four filters arranged in a 2×2 matrix. The filter unit U4 includes one B filter that passes light of the wavelength band $H_B$, diagonally arranged two Cy filters that pass light of the wavelength bands $H_B$ and $H_G$, and one W filter that passes light of the wavelength bands $H_B$, $H_G$, and $H_R$.

The W filter passes light of a white wavelength band. In other words, the W filter has sensitivity to light of the wavelength bands $H_B$, $H_G$, and $H_R$ (white light). Note that this area may be an empty (transparent) filter area instead of providing the W filter. In the third modification, under the white light imaging method, the color image generating unit 412c subtracts the blue component and green component from the white component to separate the red component.

In the filter unit U4, the number of filters that pass light of the wavelength band $H_G$ (Cy filters and W filter) is three, and the number of filters that pass light of the wavelength band $H_B$ (B filter, Cy filters, and W filter) is four.

Fourth Modification

FIG. 10 is a schematic view illustrating the configuration of the color filter according to the fourth modification of the embodiment. The color filter according to the fourth modification includes two-dimensionally arranged filter units U5 that each include 16 filters arranged in a 4×4 matrix. The filter unit U5 includes the aforementioned plurality of B filters, plurality of G filters, and plurality of Mg filters, and each G filter is diagonally arranged.

In the filter unit U5, the number of filters that pass light of the wavelength band $H_G$ (G filters) is eight, and the number of filters that pass light of the wavelength band $H_B$ (B filters and Mg filters) is eight.

Fifth Modification

FIG. 11 is a schematic view illustrating the configuration of the color filter according to the fifth modification of the embodiment. The color filter according to the fifth modification includes two-dimensionally arranged filter units U6 that each include 16 filters arranged in a 4×4 matrix. The filter unit U6 includes the aforementioned plurality of B filters, plurality of Mg filters, and plurality of W filters, and each W filter is diagonally arranged.

In the filter unit U6, the number of filters that pass light of the wavelength band $H_G$ (W filters) is eight, and the number of filters that pass light of the wavelength band $H_B$ (B filters, Mg filters, and W filters) is 16.

Note that the aforementioned color filter 202a according to the embodiment may be configured such that, in the filter unit, the number of filters that pass light of the wavelength band $H_G$ is equal to or greater than half of the number of filters that constitute the filter unit, and that the number of filters that pass light of the wavelength band $H_B$ is equal to or greater than the number of filters that pass light of the wavelength band $H_G$. Besides the aforementioned arrangement, an arrangement that satisfies the aforementioned conditions is applicable.

In the aforementioned embodiment, the color filter 202a having a plurality of filters which passes light of predetermined wavelength bands, respectively, is provided on the light-receiving surface of the image sensor 202. However, each filter may be individually provided on each pixel of the image sensor 202.

In the aforementioned endoscope apparatus 1 according to the embodiment, illumination light emitted from the illumination unit 31 is switched between white illumination light and narrow band illumination light, through the movement of the switching filter 31c with respect to the white light emitted from one light source 31a. However, two light sources that respectively emit the white illumination light and the narrow band illumination light may be switched to emit one of the white illumination light and the narrow band illumination light. When the two light sources are switched to emit one of the white illumination light and the narrow band illumination light, the aforementioned embodiment may be applied to, for example, a capsule endoscope to be introduced into a subject, the capsule endoscope including a light source unit, a color filter, and an image sensor.

In the aforementioned endoscope apparatus 1 according to the embodiment, the A/D converter 205 is provided in the distal end part 24. However, the A/D converter 205 may be provided in the processor unit 4. In addition, elements related to image processing, such as the luminance component pixel selecting unit 411, may be provided in the endoscope 2, a connector that connects the endoscope 2 and the processor unit 4, the operating unit 22, and the like. In the aforementioned endoscope apparatus 1, the endoscope 2 connected to the processor unit 4 is identified using the identification information and the like stored in the imaging information storage unit 206. However, identification means may be provided in a connection section (connector) between the processor unit 4 and the endoscope 2. For example, an identification pin (identification means) is provided on the endoscope 2 side to identify the endoscope 2 connected to the processor unit 4.

In the aforementioned endoscope apparatus 1 according to the embodiment, linear interpolation is employed as an example in which the luminance component generating unit 412a discriminates the interpolation direction and performs interpolation processing with respect to the luminance component pixel. However, interpolation processing is not limited to this example, and interpolation processing may be performed by cubic interpolation or any other nonlinear interpolation.

According to some embodiments, it is possible to obtain high-resolution images under both of the white light imaging method and the narrow band imaging method.

As described above, the endoscope apparatus according to some embodiments is useful in obtaining high-resolution images under both of the white light imaging method and the narrow band imaging method.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope apparatus comprising:
a light source configured to emit one of white illumination light and narrow band illumination light, the white illumination light including red wavelength band light, green wavelength band light, and blue wavelength band light, and the narrow band illumination light having a narrow wavelength band included in each of the blue wavelength band light and the green wavelength band light;
an image sensor having a plurality of pixels, wherein each pixel is configured to receive light, the plurality of pixels being arranged in a lattice pattern, and the image sensor being configured to perform photoelectric conversion on the light received by each of the plurality of pixels to generate an electric signal;
a color filter comprising a filter unit arranged corresponding to the plurality of pixels, the filter unit including a plurality of filters having at least a filter for passing the blue wavelength band light, and a filter for passing the blue wavelength band light and at least one of the green wavelength band light and the red wavelength band light, the number of the filters for passing the green wavelength band light being equal to or greater than half of the number of all the filters of the filter unit, and the number of the filters for passing the blue wavelength band light being equal to or greater than the number of the filters for passing the green wavelength band light; and
a hardware processor configured to:
select, from the plurality of pixels, a luminance component pixel for receiving light of a luminance component, wherein the luminance component is among a plurality of color components, and the selection of the luminance component pixel is based on a control signal indicating a type of illumination light emitted by the light source;
generate a luminance component value based on a pixel value of the selected luminance component pixel;
generate at least one color component value based on the generated luminance component value, wherein the at least one color component value correspond to color components different from the luminance component; and
generate a color image signal, based on the generated luminance component value and the generated color component values, wherein the color image signal corresponds to an image comprising pixels that includes the luminance component.

2. The endoscope apparatus according to claim 1, wherein,
when the light source emits the white illumination light, the hardware processor is configured to select, as the luminance component pixel, a pixel for receiving light via the filter for passing the green wavelength band light, and
when the light source emits the narrow band illumination light, the hardware processor is configured to select, as the luminance component pixel, a pixel for receiving light via the filter for passing the blue wavelength band light.

3. The endoscope apparatus according to claim 1, wherein the filter unit comprises a filter for passing the blue wavelength band light, and one of the green wavelength band light and the red wavelength band light.

4. The endoscope apparatus according to claim 1, wherein the color filter comprises a filter for passing the red wavelength band light, the green wavelength band light, and the blue wavelength band light.

5. The endoscope apparatus according to claim 1, wherein the hardware processor is further configured to:
generate a luminance component of a pixel other than the selected luminance component pixel based on a pixel value of the selected luminance component pixel; and
generate a color component other than the luminance component based on the luminance component generated by the hardware processor.

6. The endoscope apparatus according to claim 1, further comprising an identification information memory configured to store identification information on filter arrangement of the color filter, wherein the hardware processor is further configured to obtain information on the selected luminance component pixel based on the identification information stored in the identification information memory.

* * * * *